United States Patent [19]
Stotts et al.

[11] Patent Number: 5,161,529
[45] Date of Patent: Nov. 10, 1992

[54] CARDIAC PACEMAKER WITH CAPTURE VERIFICATION

[75] Inventors: Lawrence J. Stotts, Lake Jackson, Tex.; James P. Nelson, Manchester, Mo.

[73] Assignee: Intermedics, Inc., Angleton, Tex.

[21] Appl. No.: 278,969

[22] Filed: Dec. 2, 1988

[51] Int. Cl.$^5$ .............................................. A61N 1/362
[52] U.S. Cl. ........................................... 128/419.0 PG
[58] Field of Search .............. 128/419 PG, 696; 330/9

[56] References Cited

U.S. PATENT DOCUMENTS

| | | | |
|---|---|---|---|
| 4,261,369 | 4/1981 | Allor | 128/696 |
| 4,381,786 | 5/1983 | Duggan | 128/419 PG |
| 4,436,093 | 3/1984 | Belt | 128/419 PG |
| 4,555,668 | 11/1985 | Gregorian et al. | 330/9 |
| 5,024,221 | 6/1991 | Morgan | 128/419 PG |

*Primary Examiner*—William E. Kamm
*Assistant Examiner*—Scott M. Getzow
*Attorney, Agent, or Firm*—John R. Merkling

[57] ABSTRACT

A pacemaker having an electrical stimulation source of known type is provided with a sense amplifier having a switched capacitor circuit which allows switching of the amplifier's bandpass frequency characteristic thereby selectively varying the cardiac signal frequencies subject to sensing. The heart's electrical activity is detected in a first predetermined low frequency range after to delivery of a stimuli to detect evoked electrical activity and a second predetermined high frequency range to detect intrinsic electrical activity. The magnitude of stimuli is varied response to the detected presence or absence of evoked electrical activity.

32 Claims, 2 Drawing Sheets

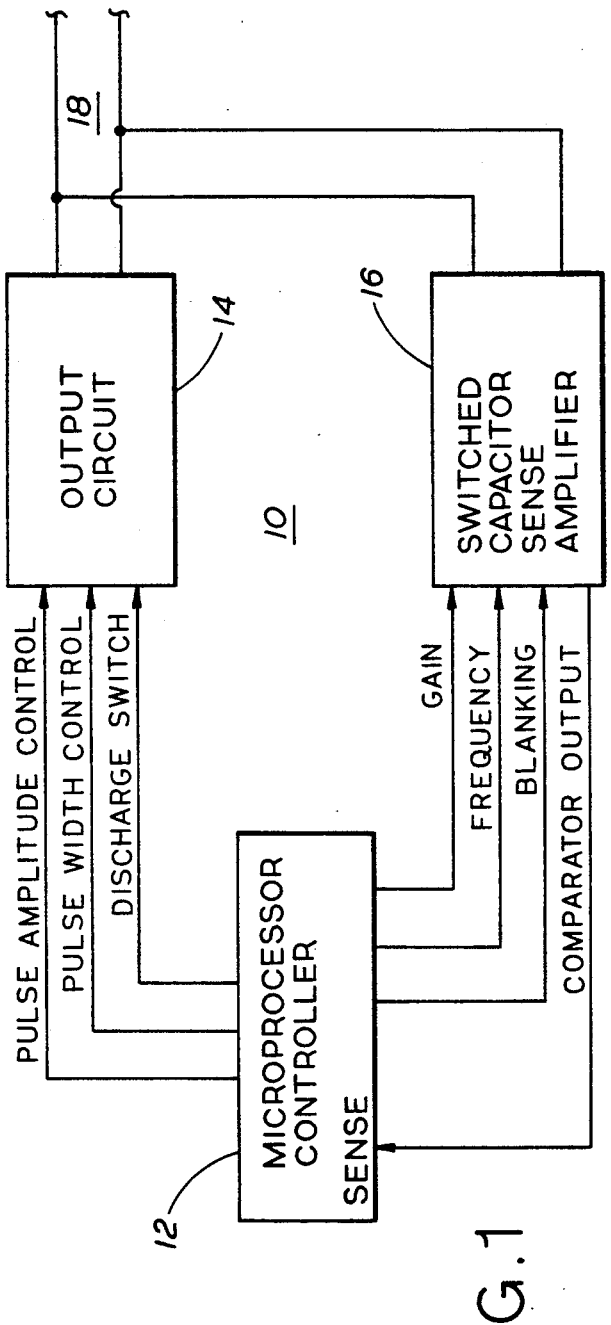
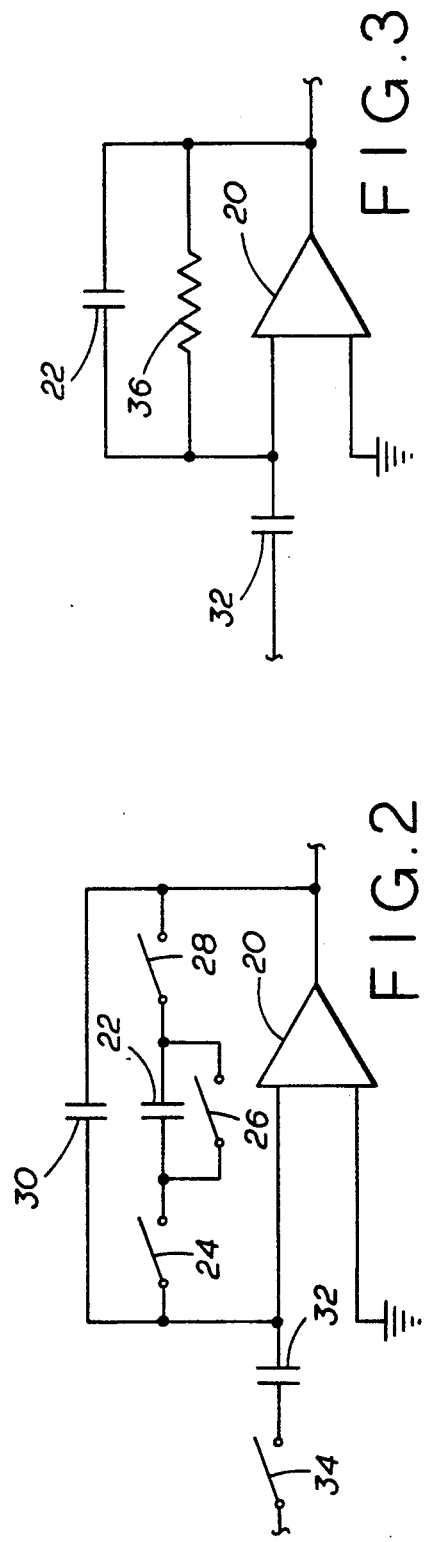

CARDIAC PACEMAKER WITH CAPTURE VERIFICATION

BACKGROUND OF THE INVENTION

1. Field of the Invention

The present invention relates generally to cardiac pacemakers, and more particularly to an implantable cardiac pacemaker including means for verifying that the pacing pulses generated by the pacemaker are producing the desired stimulation of the patient's heart.

2. Relevant Background

In the normal human heart, the sinoatrial (S-A) node, generally located near the junction of the superior vena cava and the right atrium, constitutes the primary natural pacemaker by which rhythmic electrical excitation is developed. The cardiac impulse arising from the S-A node is transmitted to the two atrial chambers, or atria, at the right and left sides of the heart. In response to this excitation, the atria contract, pumping blood from those chambers into the respective ventricular chambers, or ventricles.

The impulse is transmitted to the ventricles through the atrioventricular (A-V) node, or junction, which imposes a delay, and via a conduction system comprising the bundle of His, or common bundle, the right and left bundle branches, and the Purkinje fibers. In response, the ventricles contract, the right ventricle pumping unoxygenated blood through the pulmonary artery to the lungs and the left ventricle pumping oxygenated (arterial) blood through the aorta and the lesser arteries to the body.

The right atrium receives the venous (unoxygenated) blood from the upper part of the body (head, neck and chest) via the superior vena cava, or upper great vein, and from the lower part of the body (abdomen and legs) via the inferior vena cava, or lower great vein. The blood oxygenated by the lungs is carried via the pulmonary veins to the left atrium.

This action is repeated in a rhythmic cardiac cycle in which the atrial and ventricular chambers alternately contract and pump, then relax and fill. One-way valves along the veins, between the atrial and ventricular chambers in the right and left sides of the heart (the tricuspid valve and the mitral valve, respectively), and at the exits of the right and left ventricles (the pulmonary and aortic valves, respectively) prevent backflow of the blood as it moves through the heart and the circulatory system.

The S-A node is spontaneously rhythmic, and the cardiac rhythm originating from that primary natural pacemaker is termed "sinus rhythm". This capacity to produce spontaneous cardiac impulses is called "rhythmicity", or "automaticity". Some other cardiac tissues possess this electro-physiologic property and hence constitute secondary natural pacemakers, but the S-A node is the primary pacemaker because it has the fastest spontaneous rate. The secondary pacemakers tend to be inhibited by the more rapid rate at which impulses are generated by the sinus node.

Disruption of the natural pacemaking and propagation system occurs as a result of aging or disease, and is commonly treated by artificial cardiac pacing. Rhythmic electrical discharges of an implanted pacemaker are set at a desired rate and are applied to the heart as necessary to effect stimulation. In its simplest form, the pacemaker consists of a pulse generator powered by a self-contained battery pack, and a lead including at least one stimulating electrode electrically connected to the pulse generator. The lead is typically of the catheter type for intravenous insertion to position the stimulating electrode(s) for delivery of electrical impulses to excitable myocardial tissue in the appropriate chamber(s) in the right side of the patient's heart. Usually, the pulse generator is surgically implanted in a subcutaneous pouch in the patient's chest. In operation, the electrical stimuli are delivered to the excitable cardiac tissue via an electrical circuit that includes the stimulating and reference (indifferent) electrodes, and the body tissue and fluids.

A pacemaker operates in one of three different response modes, namely, asynchronous (fixed rate), inhibited (stimulus generated in absence of specified cardiac activity), or triggered (stimulus delivered in response to specified cardiac activity). The demand ventricular pacemaker, so termed because it operates only on demand, has been the most widely used type. It senses the patient's natural heart rate and applies stimuli only during periods when that rate falls below the preset pacing rate.

Pacemakers range from the simple fixed rate device that provides pacing with no sensing function, to the highly complex model implemented to provide fully automatic dual chamber pacing and sensing functions. The latter type of pacemaker is the latest in a progression toward physiologic pacing, that is, the mode of pacing that restores cardiac function as much as possible toward natural pacing.

Regardless of the particular type of pacemaker that may be employed to pace the patient's heart, it is essential to ascertain that the pacing pulse applied via the implanted electrode assembly is indeed stimulating the heart. That is to say, the pulse in conjunction with the implanted cathodic electrode must impress an electric field of sufficient field strength and current density on the excitable myocardial tissue at the electrode site to initiate depolarization of the tissue and the spreading of a so-called action potential. When that happens, the chamber in which the cathodic electrode is implanted undergoes contraction in the same manner as would a healthy heart under the influence of the natural physiologic pacing system. This stimulation of the heart, in which a pulse generated by a cardiac pacemaker causes contraction of the selected chamber(s) is termed "capture." The means or method by which it is ascertained that the pacemaker stimuli are achieving capture of the heart is called "capture verification."

It is a principal object of the present invention to provide a pacemaker having an improved means and method for capture verification.

In general, capture verification techniques are based on detecting the potential evoked when the heart is captured. If capture has not occurred, there will be no evoked potential. It follows that each time the heart is paced, the cardiac signal may be monitored after a suitable delay to detect the presence of the evoked potential, and thereby to verify capture. In practice, however, reliable capture verification is not quite so simple, for many reasons, some of the more important being the small amplitude of the atrial signal, the signal masking attributable to electrode polarization (a signal-to-noise problem), and the relative difference between frequencies present in the atrial and ventricular signals.

Accordingly, it is another broad object of the present invention to provide a technique for capture verification which surmounts the usual impediments to sensing the potential evoked as a result of capture.

SUMMARY OF THE INVENTION

According to the present invention, a pacemaker sense amplifier, which differs from the traditional form, is employed to detect evoked potentials. In particular, the sense amplifier comprises a switched capacitor amplifier which allows the amplifier's bandpass frequency to be switched at will, thereby selectively varying the cardiac signal frequencies subjected to sensing. The effect is to provide a sense amplifier with a programmable frequency response.

Prior to the application of a pacing stimulus to the heart, the frequency response (bandpass characteristic) of the sense amplifier is selectively set to detect cardiac activity in the form of the intrinsic QRS pattern, in the same manner as is customary with pacemakers of the prior art. However, at the moment that a stimulating pulse is delivered to the heart, the sense amplifier is switched to a lower frequency bandpass to render it more responsive to an evoked potential (for example, the T wave). After a time interval during which an evoked response to the stimulus should have been detected (the presence or absence of such a response being indicative of capture or the lack of capture, respectively), the amplifier is switched back to the original bandpass characteristic to sense the intrinsic response.

This mode of operation by the sense amplifier of the present invention serves to eliminate the capture verification problem attributable to electrode polarization, as well as to other difficulties. By utilizing a programmable, tunable amplifier the limitation of prior sense amplifiers, which required that the bandpass frequency response be designed to best provide the intrinsic signal detection, is avoided. Instead, the amplifier bandpass characteristic may be switched back and forth to selectively monitor the frequency ranges best suited t detecting the intrinsic and evoked responses.

BRIEF DESCRIPTION OF THE DRAWINGS

The above and other objects, aspects, features and advantages of the present invention will become more apparent from a consideration of the ensuing detailed description of a presently preferred embodiment thereof, taken together with the accompanying drawings, in which:

FIG. 1 is a simplified block diagram of the pulse generator or stimulus generator portion of a cardiac pacemaker depicting a microprocessor-controlled sense amplifier according to the invention;

FIG. 2 is a simplified circuit diagram of the sense amplifier of FIG. 1; and

FIG. 3 is a partial electrical equivalent to the circuit of FIG. 2.

DETAILED DESCRIPTION OF THE PREFERRED EMBODIMENT

Figure 4:
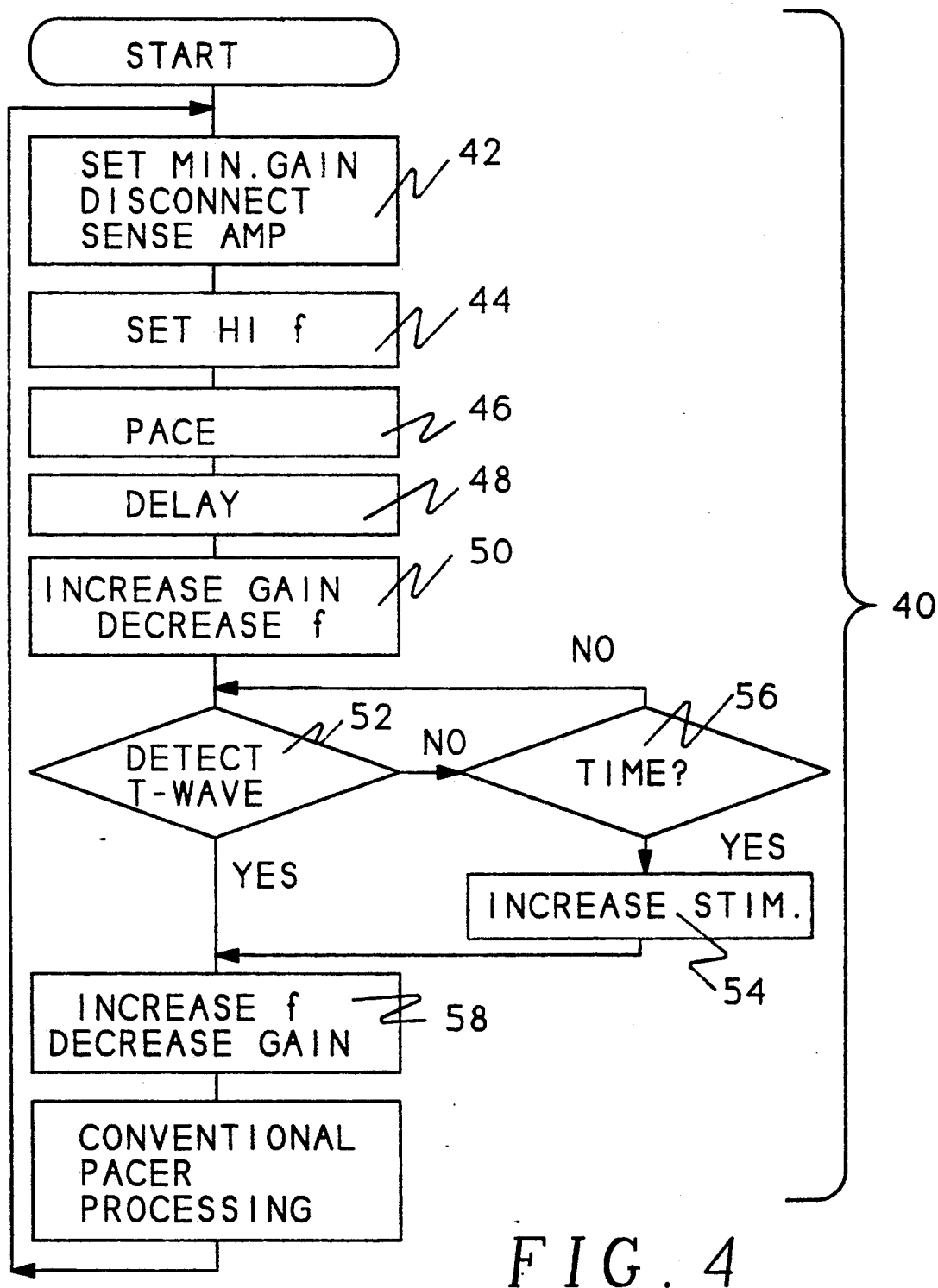
FIG. 4 is a simplified flow chart showing control of the pulse stimulus level.

Referring now to FIG. 1, a cardiac pacemaker 10 comprises an output circuit 14, a microprocessor controller 12 and a sense amplifier 16. A pair of electrodes (not shown) are coupled to output circuit 14 and sense amplifier 16 via a lead assembly 18. A bipolar configuration has been illustrated, although a unipolar configuration may alternatively be selected without departing from the spirit and scope of the subject invention.

The output circuit 14 is of any conventional type for generating stimulating pulses which are to be selectively delivered (depending on the specific nature of the pacemaker, i.e., fixed rate, inhibited or triggered, as discussed above) to the heart of the patient using the pacemaker, via the stimulating cathodic electrode of lead assembly 18 and through the return path of the body tissue and fluids and the indifferent anodic electrode (not shown). Output circuit 14 is also conventionally implemented to be controlled by microprocessor 12 in respect to the amplitude and width of each stimulating pulse, and the timing of the discharge of the capacitor(s) (not shown) contained within the output circuit after being charged to a desired energy level from pacemaker batteries (not shown) or via a known voltage multiplier circuit (also not shown).

According to the present invention, sense amplifier 16 has a programmable frequency response which is controlled by the microprocessor 12 based on signal information supplied by the latter to the sense amplifier 16 on a data bus. Prior to a pace event (i.e., the delivery of a stimulating pulse to the patient's heart), microprocessor 12 switches sense amplifier 16 to a condition of minimum gain and disconnects the sense amplifier input circuit from lead assembly 18 and, hence, from output circuit 14. This serves to avoid distortion of the sense amplifier signal and potential damage to the sense amplifier circuit from the pacing pulse (stimulus). This is illustrated in FIG. 4 at step 42. At the same time, the microprocessor 12 switches the sense amplifier 16 to a first predetermined high frequency (i.e., high bandpass) setting to assure rapid attenuation of any artifact (i.e., lead depolarization and discharge). This is step 44 in FIG. 4. This frequency range may be the same at which sense amplifier 16 is set for detecting intrinsic cardiac responses, such as the QRS complex. It may also be an even higher frequency, to more effectively blank out the pulse signal, as explained below.

The stimulating pulse is delivered (FIG. 4, step 46) to excitable myocardial tissue in the vicinity of the implanted stimulating cathodic electrode via the lead assembly 18. Now it is essential to determine whether the affected chamber has undergone contraction and whether the stimulus has captured the heart. Within a suitable delay interval (for example, 10–30 msec) following delivery of the electrical stimulus generated by output circuit 14 (FIG. 4, step 48), the microprocessor 12 controls the switching of the sense amplifier 16 to a second predetermined bandpass frequency characteristic setting, which is displaced to a lower frequency range than the first (e.g., half the original center frequency) (FIG. 4, step 50). The timing of these events may be adjusted by the microprocessor in order to optimize the result for different output amplitudes and pulse widths. The gain may also be changed by switch capacitors (not shown) in parallel with $C_{32}$ (see FIG. 2), under microprocessor control. (FIG. 4, step 50) A similar lowpass stage may be constructed using the same switching technique. The complete sense amplifier is a cascade of highpass and lowpass stages which produces a bandpass characteristic which has frequency programmability together with switching the sense amplifier to a higher gain setting, which is suitable to sense potentials evoked by the stimulus. If an evoked potential is detected (FIG. 4, step 52), capture is verified; if there is no evoked potential, the stimulus must be increased (step 54) the next time.

When the sense time programmed in the microprocessor 12 for detecting evoked potentials has elapsed (step 56), the microprocessor again controls the switching of the sense amplifier bandpass frequency characteristic to the high bandpass setting and reduces the amplifier gain setting, in preparation for detecting intrinsic cardiac signal responses (step 58).

Referring now to FIG. 2, the high pass stage for the sense amplifier 16 includes an amplifier 20, and a capacitor 22 coupled between the input and output terminals of the amplifier. Three switches 24, 26, and 28 are in circuit with capacitor 22 and are controlled by signals from the microprocessor 12 to switch the capacitor 22 at a predetermined frequency. The capacitor 22 is placed in the circuit when switches 24 and 28 on either side of it are turned on by the OA pulse waveform (to be described presently), and is shorted out when switch 26, connected across the capacitor 22, is turned on. Usually, capacitor 22 appears as a resistance 36 (as shown in FIG. 3), equal to $\frac{1}{4}fC_{22}$ where "f" is the clock switching frequency for the capacitor and "C" is the capacitance value. The highpass cut-off frequency is then equal to $\frac{1}{2} RC_F = \frac{1}{2} f (C_{22}/C_{30})$, and the flatband gain is equal to $C_{32}/C_{30}$. Switch 34 prevents signal feed-through.

In this manner, the bandpass frequency of the sense amplifier is changed at the switching rate of the capacitor, and the gain changed by connecting capacitors into and out of the circuit, both under a processor control. The shifts in amplifier gain and bandpass characteristic are discrete and, in this example, the amplifier has only two displaced frequency response settings. However, more than two can be provided by using additional capacitors and switches, although the settings in that case are limited to multiples of the clock frequency. Two different frequency bandpass characteristics are quite sufficient for purposes of capture verification according to the present invention.

A nominal setting is utilized for the normal ECG (intrinsic response), and for the interval during delivery of the pacing pulse. The bandpass is then shifted to a lower frequency range to examine the evoked response (if any) into the refractory period, and thereafter is returned to the initial bandpass characteristic constituting the nominal setting. Moreover, during blanking it would be desirable to shift the bandpass characteristic to an even higher frequency range, to effectively blank out signals, while also opening the amplifier inputs. Going to the latter high frequency range is also desirable to settle out the voltage stored on the capacitor 22.

The amplifier circuit with capacitors and switches is readily fabricated in integrated circuit form. While the switches have been shown as mechanical switches for ease of illustration, it is to be understood that solid state switching of a conventional nature would be preferred.

The time constant of the FIG. 3 circuit is $= RC$, where "R" is the effective resistance represented by the switched capacitor as described above, and "C" is the capacitance of a second capacitor 30 connected across the amplifier. If the aforementioned value of "R" is substituted for "R" in the time constant equation, it is apparent that the time constant of the circuit is the ratio of the two capacitors and the clock frequency. Since the clock frequency is crystal-controlled, and the ratio of the capacitance values may be set (and is repeatable in production) with great accuracy, a very accurate bandpass frequency setting may be achieved.

While a preferred embodiment of the invention has been described, it will be apparent to those skilled in the art to which the invention pertains, from consideration of the disclosure herein, that various modifications may be implemented without departing from the inventive principles. Accordingly, it is intended that the invention be limited only by the appended claims.

We claim:

1. An implantable cardiac pacemaker comprising:
   means for generating electrical stimuli to be selectively delivered to a patient's heart; and
   means for sensing electrical activity of said heart, said sensing means including
   at least one amplifier, and
   means for selectively changing the bandpass frequency characteristics of said amplifier during a cardiac cycle to a first predetermined low frequency range for a first period of time after delivery of a stimulus to said heart to detect evoked electrical activity in the heart and to a second predetermined high frequency range for a second period of time to detect intrinsic electrical activity in the heart.

2. The implantable cardiac pacemaker according to claim 1 further comprising means responsive to the presence or absence of evoked electrical activity for adjusting the output of said stimuli generating means.

3. The implantable cardiac pacemaker according to claim 2 wherein the means for selectively changing frequency characteristics comprises at least one capacitor and means for switching said capacitor into and out of connection with said amplifier at a selected frequency.

4. The implantable cardiac pacemaker according to claim 3 wherein said means for selectively changing the frequency characteristics further includes a microprocessor controlling said switching means.

5. The implantable cardiac pacemaker according to claim 1 further comprising means for selectively changing the gain of said amplifier to a first high gain during said first period of time and to a second low gain during said second period of time.

6. The implantable cardiac pacemaker according to claim 5 further comprising means responsive to the presence or absence of evoked electrical activity for adjusting the output of said stimuli generating means.

7. The implantable cardiac pacemaker according to claim 6 wherein the means for selectively changing frequency characteristics comprises at least one capacitor and means for switching said capacitor into and out of connection with said amplifier at a selected frequency.

8. The implantable cardiac pacemaker according to claim 7 wherein said means for selectively changing the frequency characteristics further includes a microprocessor controlling said switching means.

9. The implantable cardiac pacemaker according to claim 8 wherein said gain changing means comprise a plurality of capacitors and means for selectively connecting said capacitors to said amplifier.

10. The implantable cardiac pacemaker according to claim 9 wherein said selectively connecting means further comprises a microprocessor.

11. The implantable cardiac pacemaker according to claim 5 wherein the frequency changing means further comprises means for changing the bandpass frequency characteristics of said amplifier to a third predetermined higher frequency range for a third period of time at least immediately after delivery of said stimulus to the heart and before said first period of time.

12. The implantable cardiac pacemaker according to claim 11 further comprising means responsive to the presence or absence of evoked electrical activity for adjusting the output of said stimuli generating means.

13. The implantable cardiac pacemaker according to claim 12 wherein the means for selectively changing frequency characteristics comprises at least one capacitor and means for switching said capacitor into and out of connection with said amplifier at a selected frequency.

14. The implantable cardiac pacemaker according to claim 13 wherein said means for selectively changing the frequency characteristics further includes a microprocessor controlling said switching means.

15. The implantable cardiac pacemaker according to claim 14 wherein said gain changing means comprise a plurality of capacitors and means for selectively connecting said capacitors to said amplifier.

16. The implantable cardiac pacemaker according to claim 15 wherein said selectively connecting means further comprise a microprocessor.

17. A method for adjusting an implantable cardiac pacemaker comprising:
  generating electrical stimuli to be selectively delivered to a patient's heart,
  sensing electrical activity of said heart,
  amplifying sensed electrical activity,
  changing bandpass frequency characteristics during a cardiac cycle to a first predetermined low frequency range for a first period of time after delivery of a stimulus to said heart,
  detecting evoked electrical activity in the heart, and
  changing bandpass frequency characteristics during said cardiac cycle to a second predetermined high frequency range for a second period of time to detect intrinsic electrical activity in the heart.

18. The method for adjusting the implantable cardiac stimulator according to claim 17 further comprising adjusting the generation of said electrical stimuli responsive to the presence or absence of evoked electrical activity.

19. The method for adjusting the implantable cardiac pacemaker according to claim 18 wherein step of changing frequency characteristics comprises switching at least one capacitor into and out of connection with an amplifier at a selected frequency.

20. The method for adjusting the implantable cardiac pacemaker according to claim 19 wherein said step of changing the frequency characteristics further includes controlling said switching with a microprocessor.

21. The method for adjusting the implantable cardiac pacemaker according to claim 17 further comprising changing the gain of an amplifier to a first high gain during said first period of time and to a second low gain during said second period of time.

22. The method for adjusting the implantable cardiac stimulator according to claim 21 further comprising adjusting the generation of said electrical stimuli responsive to the presence or absence of evoked electrical activity.

23. The method for adjusting the implantable cardiac pacemaker according to claim 22 wherein the step of changing frequency characteristics comprises switching at least one capacitor into and out of connection with said amplifier at a selected frequency.

24. The method for adjusting the implantable cardiac pacemaker according to claim 23 wherein said step of changing the frequency characteristics further includes controlling said switching with a microprocessor.

25. The method for adjusting the implantable cardiac pacemaker according to claim 24 wherein said step of changing gain comprises selectively connecting at least one of a plurality of capacitors to said amplifier.

26. The method for adjusting the implantable cardiac pacemaker according to claim 25 wherein said selectively connecting step further comprises controlling selection of said capacitors with a microprocessor.

27. The method for adjusting the implantable cardiac pacemaker according to claim 21 further comprising changing the bandpass frequency characteristics of said amplifier to a third predetermined higher frequency range for a third period of time at lest immediately after delivery of said stimulus to the heart and before said first period of time.

28. The method for adjusting the implantable cardiac stimulator according to claim 27 further comprising adjusting the generation of said electrical stimuli responsive to the presence or absence of evoked electrical activity.

29. The method for adjusting the implantable cardiac pacemaker according to claim 28 wherein the step of selectively changing frequency characteristics comprises switching at least one capacitor into and out of connection with an amplifier at a selected frequency.

30. The method for adjusting the implantable cardiac pacemaker according to claim 29 wherein said step of selectively changing the frequency characteristics further includes controlling said switching of said at least one capacitor by a microprocessor.

31. The method for adjusting the implantable cardiac pacemaker according to claim 30 wherein said step of changing gain comprises selectively connecting at least some of a plurality of capacitors to said amplifier.

32. The method for adjusting the implantable cardiac pacemaker according to claim 31 wherein said step of selectively connecting further comprises controlling said capacitors with a microprocessor.

* * * * *